United States Patent [19]  [11]  4,419,819
Dickhudt et al.  [45]  Dec. 13, 1983

[54] METHOD OF MAKING BIOMEDICAL LEAD WITH LOBED LEAD ANCHOR

[75] Inventors: Eugene A. Dickhudt; Roger A. Paulson, both of New Brighton, Minn.

[73] Assignee: Medtronic, Inc., Minneapolis, Minn.

[21] Appl. No.: 344,123

[22] Filed: Jan. 29, 1982

[51] Int. Cl.³ .............................................. H01R 43/00
[52] U.S. Cl. ................................. 29/857; 128/419 D; 128/785
[58] Field of Search ................. 29/860, 861, 862, 863, 29/451, 522 R, 516, 454, 857; 128/419 P, 784, 785, 786

[56] References Cited

U.S. PATENT DOCUMENTS 3,397,699  8/1968  Kohl .............................. 29/522 R X
3,866,615  2/1975  Hewson ........................... 128/419 D
3,974,834  8/1976  Kane ............................ 128/419 P X
4,285,347  8/1981  Hess .................................. 128/785
4,374,527  2/1983  Iverson ............................... 128/785

Primary Examiner—Howard N. Goldberg
Assistant Examiner—Carl J. Arbes
Attorney, Agent, or Firm—Robert J. Klepinski; John L. Rooney; Joseph F. Breimayer

[57] ABSTRACT

A length of tubing having an inside diameter equal to the diameter of a biomedical lead is slit along a direction parallel to its axis, with the length of the slits being equal to the desired circumference for lead anchor lobes. The tubing is slipped over the lead body and compressed so that the slit portions of the body expand into lobes, and while the tubing is compressed its ends are heated and compressed until they fuse to the lead body.

5 Claims, 4 Drawing Figures

METHOD OF MAKING BIOMEDICAL LEAD WITH LOBED LEAD ANCHOR

BACKGROUND OF THE INVENTION

1. Field of the Invention

This invention in general relates to the field of leads for the electrical stimulation of living tissue, and more particularly concerns a method of making a lead having a lobed lead anchor that permits large numbers of high quality leads to be produced in relatively short periods of time.

2. Description of the Prior Art

Electrical stimulation of the body is an increasingly important medical procedure. In this medical context the stimulating lead comprises a conductor covered by a pliable insulating material which is resistant to body fluids and an exposed electrode electrically connected to the conductor. Often the lead includes a means for anchoring the electrode and the lead in the tissue to be stimulated. One type of such a lead anchor comprises semicircular lobes formed in or attached to the lead body.

U.S. patent application Ser. No. 926,100 filed July 19, 1978 now U.S. Pat. No. 4,374,527 issued Feb. 22, 1983 on an invention of a Alfred A. Iverson, U.S. Pat. No. 4,154,247 on a invention of Edward G. O'Neill, U.S. Pat. No. 3,866,615 on an invention of John R. Henson, and U.S. Pat. No. 4,285,347 on an invention of Stanley R. Hess all disclose lobed lead anchors. The lobes in these prior art leads are formed either by injection molding, or as in U.S. Pat. No. 4,154,247 by heating the lead in boiling water and forming the lobe by hand. The injection molding method is quite slow and expensive, since the number of lead achors that can be made is limited by the number of molds available, and each mold must be assembled, filled, allowed to cool and then disassembled. The hand molding method, while being somewhat faster and cheaper does not lend itself to reproducability and high quality. Thus, a method of manufacture that would permit leads of the quality and reproducabilty obtainable with the injection molding method to be produced with speed and simplicity of the hand molding method.

SUMMARY OF THE INVENTION

It is an object of the invention to provide a method of manufacturing a lobed biomedical stimulation lead that is significantly faster than prior methods of manufacture.

It is also an object of the invention to provide a method of manufacturing a lobed biomedical stimulation lead which has the reproducability and high quality of the injection molded lead, yet is not limited by the number of molds available or by the mold curing time.

It is a further object of the invention to provide a method of manufacturing a lobed biomedical stimulation lead that achieves one or more of the above objects and which, at the same time, is relatively inexpensive.

The method of manufacture, according to the invention, comprises providing a length of tubing longer than the length of the lobes desired and shorter than the lead, having an inside diameter substantially equal to the outside diameter of the lead body at the position it is desired to locate the lobed lead anchor, and having a plurality of slits in the tubing along a direction substantially parallel to the axis of the tubing, with each slit extending from a point distal from the proximal end of the tubing to a point proximal from the distal end of the tubing, and having a slit length equal to the desired semicircular circumference of the lobe. The tubing is slipped over the lead body and located at the position at which the lead anchor is desired. The tubing is compressed in a direction parallel to its axis thereby expanding the slit portion of the tubing into lobes, and while the tubing is in the compressed condition it is secured to the lead body at at least one point proximal to the lobes and at least one point distal to the lobes. Preferably, the tubing is secured to the lead body by heating the ends of the tube and compressing them against the lead body until they fuse to the lead body. Since all of the above steps can be completed in seconds as compared to the hours required for molding and curing processes, this methods lends itself to the production of large numbers of quality lobed leads over any given manufacturing period, as compared to prior art manufacturing methods. Numerous other features, objects and advantages of the invention will become apparent from the following detailed description when read in conjunction with the accompanying drawings.

DESCRIPTION OF THE PREFERRED EMBODIMENT

Figure 1:
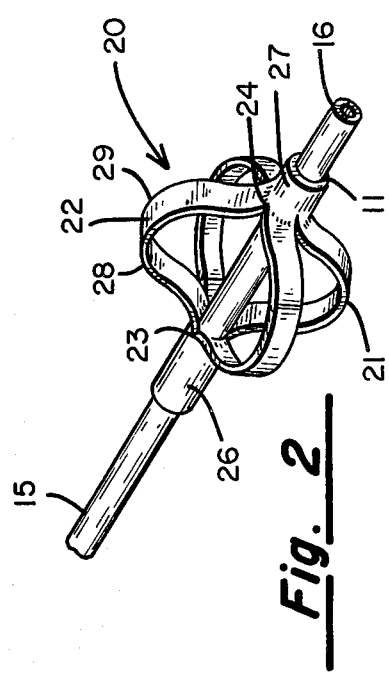
FIG. 1 shows a length of tubing as provided in the method of manufacture.
Figure 2:
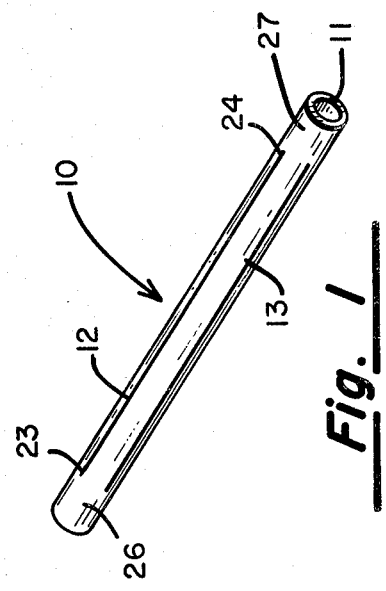
FIG. 2 shows the tubing of FIG. 1 compressed in place on the lead casing.
Figure 3:
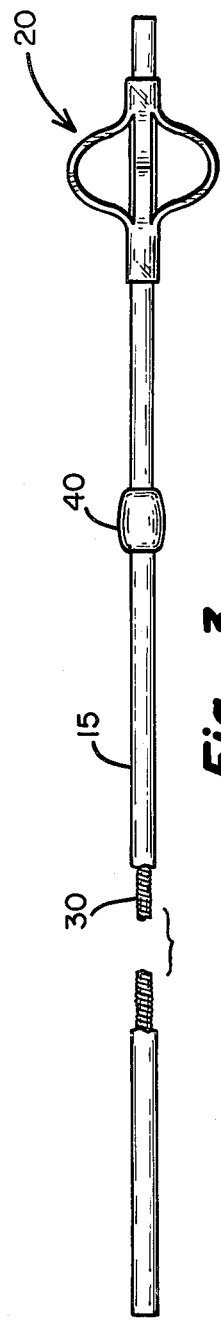
FIG. 3 shows an exemplarary lead as manufactured according to the invention.

A tube 10 is provided in the method of the invention as shown in FIG. 1. The tube is slipped over a lead casing and compressed as shown in FIG. 2, and then secured to the lead casing. A complete electrode including conductor 30 and electrode 40 is shown in FIG. 3. The conductor 30 may be inserted into casing 15 and electrode 40 may be secured to casing 15 either before or after lobed lead anchor 20 is secured to the casing 15. The method of inserting conductor 30 and securing electrode 40 is conventional and shall not be discussed further herein.

Proceeding now to a more detailed description of the method according to the invention, the tube 10 provided (FIG. 1) is of a length longer than the circumference of the lobes desired and has an inside diameter 11 substantially equal to the outside diameter of the lead casing at the position it is desired to locate the lead anchor. "Circumference of the lobes" means the (approximately) semicircular circumference of one of the four lobes as shown in FIG. 2, for example, the circumference of lead 22 from point 23 to point 24. In the preferred embodiment shown, the length of tube 10 is chosen to be about ⅛ inch longer than the circumference of one of the lobes. The length of tube 10 may be any length up to to the length of the lead and still come within the concept of the invention, although the shorter lengths as described above are preferred. Preferably the inside diameter 11 of tube 10 is a small amount, for example 0.002 inches, smaller than the outside diameter 16 of casing 15, since this makes the fit of tube 10 on casing 16 tighter. However, any inside diameter 11 equal to the outside diameter 16 plus or minus about 0.01 inches may be used, since the materials out of which the tube 10 and casing 15 are made are pliable enough to take up the difference.

For purposes of this discussion, the upper lefthand portion of tube 10 in FIG. 1 will be considered to be the proximal end of the tube, while the lower righthand end will be considered to be the distal end of the tube. This corresponds to the conventional labeling of the ends of the lead; i.e., the end closest to the pulse generator (not shown) is generally labeled the proximal end while the end closest to the electrode is labeled the distal ends. Slits such as 12 and 13 are made along the length of tube 10 in a direction parallel to the axis of the tube. The precise length of the slit is not critical, but it should not extend to either of the ends. Stated in a positive manner, the slits in tube 10 extend from a point 23 distal from the proximal end of the tubing to a point 24 proximal from the distal end of the tubing. Preferably, all the slits such as 12 and 13 will be of equal length. This length will be equal to the circumference of the lobes such as 22. The unslit ends 26 and 27 of tube 10 are preferably each about 1/16 inch in length, although as discussed above they may be longer or shorter.

The tube 10 provided is slipped over lead casing 15 and positioned at a location corresponding to the position at which it is desired to have a lead anchor. The tube 10 is then compressed in a direction parallel to its axis, expanding the slit portions of the tube into lobes, such as 22, thus transforming the tube 10 into lobed lead anchor 20. While the tube 10 is in the compressed position, the ends 26 and 27 are secured to the lead casing 15. Preferably they are secured by heat swaging, that is a cylindrical press or tool that fits about the ends 26 and 27 is heated and compressed about the ends until they fuse with casing 15. Preferably, the press or tool is heated to about 300° F.

Athough four lobes are shown in the preferred embodiment, any number of lobes which it is physically possible to make in the tubing 10 may be used, however. Generally the number of lobes such as 22 will be equal to the number of slits such as 12 and 13 made.

Tube 10 is preferably made of the same material as casing 15, which preferably is polyurethane but may be any other material sufficiently pliable and resistant to body fluids, such as silicone rubber, etc.

Figure 4:
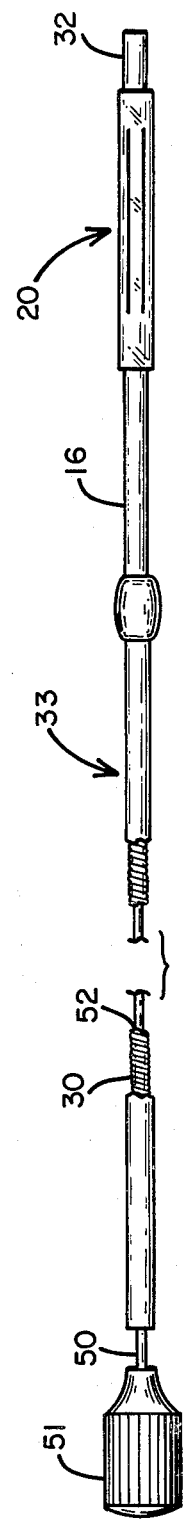
FIG. 4 shows the lead of FIG. 3 with a stylet inserted illustrating one of the advantages of the invention.

A feature of the invention is illustrated in FIGS. 3 and 4. As discussed in the prior art patents mentioned in the Background of the Invention, biomedical leads are generally implanted in the human body by inserting the lead through a Touhy needle. In order to more easily insert the lead in the needle, a stiff stylet wire 50 attached to stylet handle 51 is inserted in a central lumen 52 in conventional coil conductor 30. The stylet stops at the closed end 32 of lead body 33. The force of the stylet on the end 32 of lead body 33 stretches out the lead body in the area of the lead anchor 20 which causes the lead anchor 20 to return to the tube shape (See FIG. 4). This allows the lead anchor to pass easily through the Touhy needle. After the lead anchor is within the body cavity, the stylet wire 50 is removed and the lead anchor then reexpands to the lobed form as shown in FIG. 3. The method of manufacture as described above places an outward tending tension in lobes such as 22 and a corresponding inward-tending tension in casing 15. The outward-tending tension in lobes 20 causes them to naturally fall into the tube shape when casing 15 forming part of lead body 33 is stretched by the stylet. This tendency of the lobes such as 21 and 22 to lay flat in this state significantly enhances the ability of the doctor to pass the lead according to the invention through the Touhy needle as compared to lobed lead anchors formed by other methods, which may result in somewhat skewed, unequal, or incomplete contractions of the lobes upon stretching of the casing 15.

In the exemplary embodiment of the invention, casing 15 has an inner diameter of from about 0.020 inches to about 0.025 inches and outside diameter of about 0.035 inches. Tube 10 has an internal diameter of about 0.033 inches and an external diameter of about 0.045 inches. This exemplary embodiment is particularly suited for implantation in the epidural space.

There has been described a novel method of manufacture of a biomedical stimulation lead having a lobed lead anchor that provides for the fast and cheap manufacture of a high quality lead having a lobed lead anchor that may be more easily passed through a Touhy needle than prior art leads, and has numerous other advantages. While the invention has been described in connection with a particular embodiment, one skilled in the art will appreciate that numerous other embodiments of the method and departures from the embodiments may be made without departures from the inventive concepts. For example, the steps may be performed in any reasonable order; for instance it is possible to perform the step of compressing before the step of slipping, or other steps may be inserted to improve the method in one form or another, or to adapt the method for biomedical leads other than epidural leads. A wide variety of material other than those described, and a wide variety of dimension for the elements may be employed, while still employing the inventive elements. It is therefore to be understood that, within the scope of the appended claims, the invention be practised other than as has been specifically described.

What is claimed is:

1. A method of making a body implantable lead of the type having an exposed electrode attached to a lead body comprising a conductor connected to said electrode and an insulating casing enclosing said conductor, and a lead anchor having lobes attached to said lead casing, comprising the steps of:

providing a tube of pliable material substantially inert to body fluids, said tube being longer than the length of lobes desired and shorter than said lead body, having an inside diameter substantially equal to the outside diameter of the lead casing at the position it is desired to locate said lead anchor and having a plurality of slits in said tube in a direction substantially parallel to the axis of the tube, each slit extending from a point distal from the proximal end of the tube to a point proximal from the distal end of the tube and having a slit length equal to the lobe circumference desired;

slipping said tube over said lead casing and positioning it at the location at which the lead anchor is desired;

compressing the tube in a direction parallel to its axis to expand the slit portion of the tube into lobes; and while the tubing is in said compressed condition, securing said tubing to said lead casing at at least one point proximal to said slits and at least one point distal to said slits.

2. A method as in claim 1 wherein said step of providing comprises providing a tube having n slits wherein n is equal to the number of lobes desired.

3. The method of claim 1 wherein the step of securing comprises heating and compressing said points on the tubing to fuse the points to the lead case.

4. A method of making a body implantable lead having a lobed lead anchor, comprising the steps of:
providing a lead body having a lead casing;
providing a tube of pliable material substantially inert to bodily fluids, the tube being shorter than the lead body and having an inside diameter substantially equal to an outside diameter of the lead casing;
slitting the tube a plurality of times in a direction substantially parallel to a longitudinal axis of the tube, each slit extending from a point distal from a proximal end of the tube to a point proximal from a distal end of the tube;
slipping the tube over the lead casing to a location at which the lead anchor is desired;
compressing the tube in a direction parallel to its longitudinal axis by moving its proximal and distal ends toward each other, thereby expanding slit portions of the tube into lobes; and
while the tube is in its compressed condition, securing the ends of the tube to the lead casing.

5. The method of claim 4 wherein the step of securing comprises compressing the ends of the tube against the lead casing and heating them to fuse the ends to the lead casing.

* * * * *